(12) United States Patent
Miller et al.

(10) Patent No.: US 9,302,238 B2
(45) Date of Patent: Apr. 5, 2016

(54) NITRIC OXIDE GENERATION, DILUTION, AND TOPICAL APPLICATION APPARATUS AND METHOD

(71) Applicant: Genosys, Inc., Orem, UT (US)

(72) Inventors: J. W. Randolph Miller, Orem, UT (US); John J. Miller, Orem, UT (US); Stephen H. Fairbanks, Orem, UT (US)

(73) Assignee: SYK TECHNOLOGIES, LLC, Newport Beach, CA (US)

( * ) Notice: Subject to any disclaimer, the term of this patent is extended or adjusted under 35 U.S.C. 154(b) by 0 days.

(21) Appl. No.: 14/194,977

(22) Filed: Mar. 3, 2014

(65) Prior Publication Data

US 2014/0314880 A1 Oct. 23, 2014

Related U.S. Application Data

(63) Continuation of application No. 13/197,695, filed on Aug. 3, 2011, now Pat. No. 8,685,467.

(60) Provisional application No. 61/370,214, filed on Aug. 3, 2010.

(51) Int. Cl.
*A61K 33/00* (2006.01)
*B01J 7/00* (2006.01)

(52) U.S. Cl.
CPC ... *B01J 7/00* (2013.01); *A61K 33/00* (2013.01)

(58) Field of Classification Search
None
See application file for complete search history.

(56) References Cited

U.S. PATENT DOCUMENTS

| | | | |
|---|---|---|---|
| 4,778,450 A * | 10/1988 | Kamen | 604/65 |
| 5,045,292 A * | 9/1991 | Ruegg et al. | 423/235 |
| 5,427,797 A | 6/1995 | Frostell et al. | |
| 5,692,495 A * | 12/1997 | Sheu | 128/203.12 |
| 5,713,349 A | 2/1998 | Keaney | |
| 5,823,180 A | 10/1998 | Zapol et al. | |
| 5,839,433 A | 11/1998 | Higenbottam | |
| 5,873,359 A | 2/1999 | Zapol et al. | |
| 6,000,403 A | 12/1999 | Cantwell | |
| 6,019,100 A | 2/2000 | Alving et al. | |
| 6,063,407 A | 5/2000 | Zapol et al. | |
| 6,131,572 A | 10/2000 | Heinonen | |
| 6,142,147 A | 11/2000 | Head et al. | |
| 6,149,606 A | 11/2000 | Alving et al. | |
| 6,432,077 B1 | 8/2002 | Stenzler | |
| 6,458,109 B1 | 10/2002 | Henley et al. | |
| 6,572,594 B2 | 6/2003 | Satterfield et al. | |
| 6,581,599 B1 | 6/2003 | Stenzler | |
| 6,601,580 B1 | 8/2003 | Bloch et al. | |
| 6,612,306 B1 | 9/2003 | Mault | |
| 6,670,323 B1 | 12/2003 | Looker et al. | |
| 6,786,217 B2 | 9/2004 | Stenzler | |
| 6,793,644 B2 | 9/2004 | Stenzler | |
| 7,017,573 B1 | 3/2006 | Rasor et al. | |
| 7,040,313 B2 * | 5/2006 | Fine et al. | 128/203.12 |
| 7,045,152 B2 | 5/2006 | Stamler | |
| 7,122,018 B2 | 10/2006 | Stenzler et al. | |
| 2003/0064028 A1 * | 4/2003 | Fine et al. | 424/43 |
| 2005/0214193 A1 * | 9/2005 | D'Ottone | 423/405 |
| 2006/0172018 A1 * | 8/2006 | Fine et al. | 424/718 |
| 2010/0003349 A1 * | 1/2010 | Miller et al. | 424/718 |

FOREIGN PATENT DOCUMENTS

WO 2006/110923 10/2006
WO 2007/057763 5/2007

* cited by examiner

*Primary Examiner* — Robert A Wax
*Assistant Examiner* — Olga V Tcherkasskaya
(74) *Attorney, Agent, or Firm* — Pate Baird, PLLC (57) ABSTRACT

An apparatus for controlled delivery of nitric oxide. A pump draws air through an activated carbon filter and into a reaction chamber. The generation of nitric oxide occurs in the reaction chamber. A second pump draws the gas in the reaction chamber through a calcium hydroxide filter and delivers the nitric oxide through an orifice, or aperture, that controls the flow of nitric oxide delivered. The nitric oxide is filtered through a calcium hydroxide filter just prior to being made available for various nitric oxide therapies. Topical applications that provide a nitric oxide therapy to a surface are also provided.

10 Claims, 5 Drawing Sheets

NITRIC OXIDE GENERATION, DILUTION, AND TOPICAL APPLICATION APPARATUS AND METHOD

RELATED APPLICATIONS

This application is a continuation of U.S. patent application Ser. No. 13/197,695, filed Aug. 3, 2011 and entitled NITRIC OXIDE GENERATION, DILUTION, AND TOPICAL APPLICATION APPARATUS AND METHOD, which claims the benefit of U.S. Provisional Patent Application Ser. No. 61/370,214, filed Aug. 3, 2010 and entitled NITRIC OXIDE GENERATOR AND DILUTION APPARATUS AND METHOD, both of which are incorporated herein by reference in their entirety.

BACKGROUND

1. The Field of the Invention

This invention relates generally to chemical reactors, and more specifically to apparatus and methods for generating nitric oxide.

2. Background

The discovery of certain nitric oxide effects in live tissue garnered a Nobel prize. Much of the work in determining the mechanisms for implementing, and the effects of, nitric oxide administration are reported in literature. In its application however, introduction of nitric oxide to the human body has traditionally been extremely expensive. The therapies, compositions, preparations, hardware, and controls are sufficiently complex, large, and expensive to inhibit more widespread use of such therapies.

What is needed is a comparatively simple, easily controlled, and consequently inexpensive mechanism for introducing nitric oxide in a variable concentration. Also, needed is a simple introduction method for providing nitric oxide suitable for inhaling. Also, needed is a simple method for topical application of a nitric oxide therapy. User control and administration would be a great benefit from simplicity and reduction in size.

It would be an advance in the art to provide a generator suitable for administration of nitric oxide gas at variable concentrations. It would be an advance in the art to provide not only an independence from bottled gas, but independence from auxiliary power required for heat, pumping, instrumentation, controls, and the like.

It would be an advance in the art to provide a medium and method for topical administration of nitric oxide gas. It would be an advance in the art to provide the antimicrobial, therapeutic, and analgesic benefits of nitric oxide through a topical application.

BRIEF SUMMARY OF THE INVENTION

In accordance with the foregoing, certain embodiments of apparatus and methods in accordance with the invention provide a reactor system that produces nitric oxide and regulates the flow and concentration of nitric oxide delivered. Nitric oxide may thus be introduced into the breathing air of a subject in a controlled manner. Nitric oxide amounts may be engineered to deliver a therapeutically effective amount on the order of a comparatively low hundreds (e.g., 100-500) of parts per million, or in thousands of parts per million.

For example, sufficient nitric oxide may be presented through nasal inhalation to provide approximately five thousand parts per million in breathing air. This may be diluted due to additional bypass breathing, through nasal inhalation, or through oral inhalation.

One embodiment of an apparatus and method in accordance with the present invention may rely on a small reactor and a system of filters and pumps configured to provide a constant, regulated flow of nitric oxide. Other embodiments may provide an automated feedback system that monitors, controls, and adjusts the concentration of nitric oxide delivered.

Reactive compounds may be appropriately combined dry or in liquid form. Reactants may include potassium nitrite, sodium nitrite or the like. The reaction may begin upon introduction of heat. Heat may be initiated by liquid transport material to support ionic or other chemical reaction in a heat device.

An apparatus and method in accordance with the invention may include an insulating structure, shaped in a convenient, compact, efficient configuration such as a rectangular box, a cylindrical container, or the like. The insulating container may be sealed either inside or out with a containment vessel to prevent leakage of liquids therefrom. Such a system may not need to be constructed to sustain nor contain pressure. However, in certain embodiments, the reactor may need to be constructed to sustain and contain pressure.

In certain embodiments, chemical heaters may include metals finely divided to readily react with oxygen or solid oxidizers. Inside the containment vessel may be positioned heating elements such as those commercially available as chemical heaters. Various other chemical compositions of modest reactivity may be used to generate heat readily without the need for a flame, electrical power, or the like.

Above the heating element or heater within the containment vessel may be located a reactor. The reactor may preferably contain a chemically stable composition for generating nitric oxide. Such compositions, along with their formulation techniques, shapes, processes, and the like are disclosed in U.S. patent application Ser. No. 11/751,523, U.S. patent application Ser. No. 12/361,123, U.S. patent application Ser. No. 12/361,151, U.S. patent application Ser. No. 12/410,442, U.S. patent application Ser. No. 12/419,123, and U.S. Pat. No. 7,220,393, all incorporated herein by reference in their entireties as to all that they teach.

The reactor may include any composition suitable for generating nitric oxide by the activation available from heat. The reactor may be substantially sealed except for an inlet, such as a tubular member secured thereto to seal a path for entry of filtered air into the reactor, and an outlet, such as a tubular member secured thereto to seal a path for exit of nitric oxide from the reactor. The reactor may also include a structure to dissipate heat away from the reaction and facilitate the complete use of the reactants in the reactor.

In certain embodiments, a system of filters and pumps introduces air into the reactor and then conducts a controlled flow of nitric oxide out of the reactor. Accordingly, a system may include filters and pumps to introduce air into the reactor, control production of nitric oxide in the reactor, and conduct nitric oxide out of the reactor. The system may include devices controlling the pumps and the flow of nitric oxide.

Ultimately, an apparatus in accordance with the invention may include a cover through which an outlet penetrates from the reactor in order to connect to a cannula. This has been done effectively. The cover may also vent steam generated by the heaters in the presence of the water typically used to activate such heaters.

The system may be configured for continual use by replenishing the reactants and replacing other components as needed. Alternatively, the system may be completely wrapped in a pre-packaged assembly. In one embodiment, a heat-shrinkable wrapping material may be used to seal the outer container of an apparatus in accordance with the invention. Thus, this system may be rendered tamper-proof, while also being maintained in integral condition throughout its distribution, storage, and use.

In accordance with the foregoing, certain embodiments of an apparatus and method in accordance with the invention provide a topical medium that produces nitric oxide and provides a therapeutic concentration of nitric oxide delivered to a surface. Nitric oxide may thus be introduced to the skin, or a wound, of a subject in a controlled manner. Nitric oxide amounts may be engineered to deliver a therapeutically effective amount on the order of from comparatively low hundreds (e.g., 100-500) of parts per million, up to thousands of parts per million. For example, sufficient nitric oxide may be presented through topical application to provide approximately five hundred parts per million to the surface of a subject's skin.

One embodiment of an apparatus and method in accordance with the present invention may rely on equal amounts of a nitrite medium and an acidified medium formulated to provide a burst of nitric oxide, as well as a continuous amount of nitric oxide over a period of time. One embodiment of an apparatus and method in accordance with the present invention may provide a therapeutically effective amount of nitric oxide from a gel medium, which provides a therapeutically effective dose of nitric oxide over a relatively shorter length of time, from approximately thirty minutes up to about 3 hours.

One embodiment of an apparatus and method in accordance with the present invention may provide a therapeutically effective amount of nitric oxide from a lotion medium, which provides a therapeutically effective dose of nitric oxide over a relatively longer length of time, from about one hour up to about 6 hours. Reactants may include potassium nitrite, sodium nitrite or the like. The reaction may begin upon combination of the nitrite medium and the acidified medium.

An apparatus and method in accordance with the invention may be used for a variety of purposes, including without limitation, disinfecting and cleaning surfaces, increasing localized circulation, facilitating healing and growth, dispersing biofilms, and providing analgesic benefits.

BRIEF DESCRIPTION OF THE DRAWINGS

The foregoing features of the present invention will become more fully apparent from the following description, taken in conjunction with the accompanying drawings. Understanding that these drawings depict only typical embodiments of the invention and are, therefore, not to be considered limiting of its scope, the invention will be described with additional specificity and detail through use of the accompanying drawings in which.

DETAILED DESCRIPTION OF THE PREFERRED EMBODIMENTS

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention, as claimed, but is merely representative of various embodiments of the invention. The illustrated embodiments of the invention will be best understood by reference to the drawings.

Figure 1:
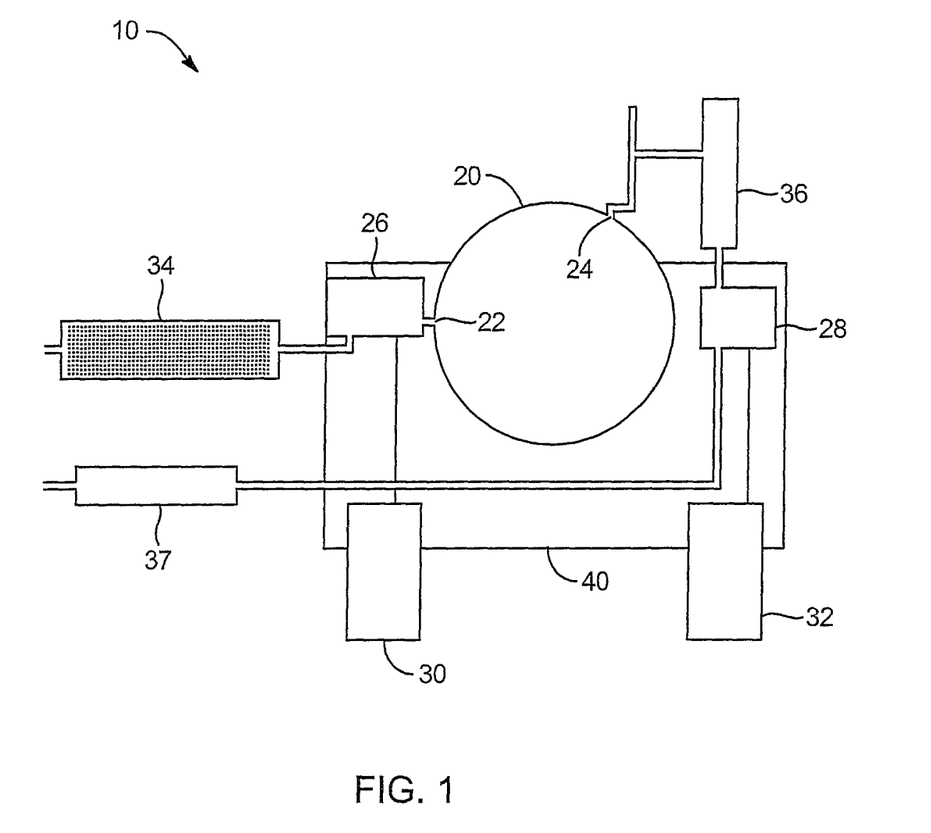
FIG. 1 is a schematic view of one embodiment of an apparatus in accordance with the invention to generate nitric oxide and control the flow and concentration of nitric oxide delivered.

Referring to FIG. 1, a nitric oxide generator 10 may include a first pump 26 that draws air through an activated carbon filter 34 and pressurizes the reaction chamber 20, or reactor 20. The pump 26 provides filtered air for dilution with the nitric oxide to be generated. The pump 26 pumps air into the reactor 20 and pressurizes the reactor 20. Any device suitable for pumping air into and pressurizing the reactor 20 may be utilized.

The pump 26 may be controlled by a potentiometer 30, or the like. Using a potentiometer 30 allows the voltage to the pump 26 to be varied according to the desires of the user. The potentiometer 30 may include circuit boards that control the speed of the pump 26. Also, pump controls that control and measure the amperage to the pumps as opposed to the voltage may also be utilized when measuring the amperage is simpler, easier, or more useful for controlling the pump speed and power. Any device suitable for controlling the pump may be utilized.

The activated carbon filter 34 filters out oxygen and moisture from the inlet air. Again, any suitable device may used to filter the inlet air appropriately. In another embodiment, the first pump 26 may pump air through the activated carbon filter 34 and then into the reaction chamber 20.

A reaction chamber 20 provides a suitable container for the reaction that produces the nitric oxide. The reaction chamber 20 can be of any suitable size or shape. The various configurations for a suitable reaction chamber 20, as well as the compounds and components used in the reaction, are described elsewhere hereinafter. However, compactness for portability and home use may be valuable.

A vent, or outlet 24, in the reaction chamber 20 allows air and nitric oxide to be drawn out of the reaction chamber 20. The outlet 24 may be configured to release excess pressure in the reaction chamber 20 by allowing air and nitric oxide to escape the system to the atmosphere. The outlet 24 may also be configured to direct the air and nitric oxide from the reactor to a first calcium hydroxide filter 36. The outlet 24 allows venting of the flow through the reactor and helps make sure the proper flow goes through the orifice. The system may provide means for applying a constant flow to the orifice and then venting overboard any remaining or excess flow of nitric oxide.

A second pump 28 draws air and nitric oxide through the first calcium hydroxide filter 36 away from the reaction chamber 20 for use in any type of nitric oxide therapy. The pump 28 further dilutes the nitric oxide with filtered air. The pump 28 may be controlled by a second potentiometer 32, or the like. Using a potentiometer allows the voltage to the pump 28 to be varied according to the desires of the user. The potentiometer may include circuit boards that control the speed of the pump. Also, pump controls that control and measure the amperage delivered to the pumps as opposed to controlling the voltage as described above. Any device suitable for controlling the pump may be utilized. The calcium hydroxide filter 36 absorbs or otherwise filters out moisture and scavenges nitrogen dioxide ($NO_2$) from the outlet air. Again, any other suitable device may used to filter or otherwise clean the outlet air appropriately.

A line from the second pump 28 is used to conduct nitric oxide away from the reactor 20 and deliver the nitric oxide for use in various nitric oxide therapies. An orifice at one end of this line is used to restrict and control the flow of nitric oxide. The nitric oxide travels from the second pump 28 through this line, through the orifice, and through a second calcium hydroxide filter 37.

This line from the second pump to the orifice may be a ⅛ inch stainless steel line that carries gas and resists heat and corrosion. Any line used in this system may be a stainless steel line that carries gas and resists heat and corrosion, or any suitable device or material that can conduct the flow of gas in an acceptable manner. Also, any line in the system may be of silicone tubing that is resistant to heat, alcohol, and castor oil. Moreover, any line in the system may be composed of any material that is suitable for the intended purpose, including without limitation, stainless steel, medical grade silicone, plastic, or the like.

The orifice used to restrict and control the flow of nitric oxide may have an aperture from about 2 to about 10 mils, and typically about 0.004 inches in diameter. Any suitable aperture that will restrict and control (e.g., effectively meter) the flow of nitric oxide at a desired level. For example, orifice or aperture may typically be of any size from approximately 0.003 inches to 0.009 inches in diameter.

Finally, the second calcium hydroxide filter 37 removes any remaining moisture and nitrogen dioxide from the gas exiting the reactor 10. After passing through this second calcium hydroxide filter 37, the nitric oxide is ready for use with any variety of nitric oxide therapies. Also, the nitric oxide may be diluted with the air delivered to the patient.

The nitric oxide reactor 10 may include a cover 40 to contain the components of the reactor. The cover 40 may be any suitable shape and material and may be designed to allow access to the components of the reactor 10. The cover 40 may also be designed to enclose a reactor 10 intended for a single use by a patient. Such a single use reactor may be discarded or returned to an appropriate facility for recycling the reactor and its components.

Figure 2:
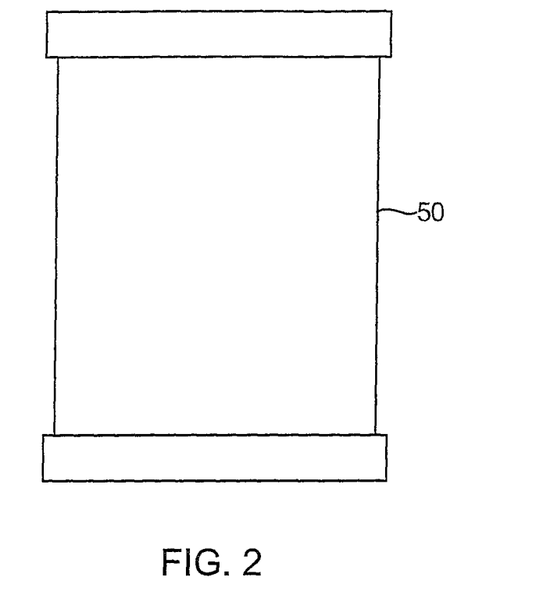
FIG. 2 is a perspective view of a containment vessel, or cannister.

Referring to FIG. 2, in one embodiment the reaction chamber 20 may be contained within a containment vessel 50, or cannister 50. The top of the containment vessel 50 may be configured to be secured, such as by being screwed on to the containment vessel 50, to close or seal the reaction chamber, or unscrewed to allow access to the reaction chamber. The containment vessel may be heated by any suitable heating element. The containment vessel may be of any suitable configuration and may be made of any suitable material, such as stainless steel.

Figure 3:
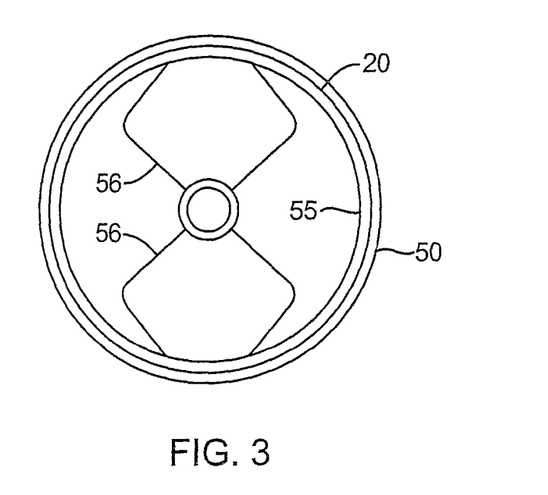
FIG. 3 is a top perspective view of an open containment vessel, or cannister.

Referring to FIG. 3, in one embodiment the reaction chamber 20 may include fins 56, fin-like structures 56, in contact with the heating element 58 of the reaction chamber 20 and the outside wall 55 of the reaction chamber 20. These fins 56 dissipate the heat of the reaction and facilitate a complete nitric oxide reaction and use of all the reactants. These fins 56 may be composed of any serviceable heat transfer material that will not interfere with the reaction in the reactor and will stay in contact with the heating element 58 and the outside wall 55 of the reactor. Fins 56 may be designed to provide a constant contact force between the heater in the reactor and the wall of the reaction chamber 20. Fins 56 may be intimately bonded or may be described as "spring-loaded" fins in forced contact with the walls of the reaction chamber 20. The fins 56 are especially helpful when the reactants for the nitric oxide reaction include a powder, in which conductive heat transfer through the reactants is comparatively poor.

Figure 4A:
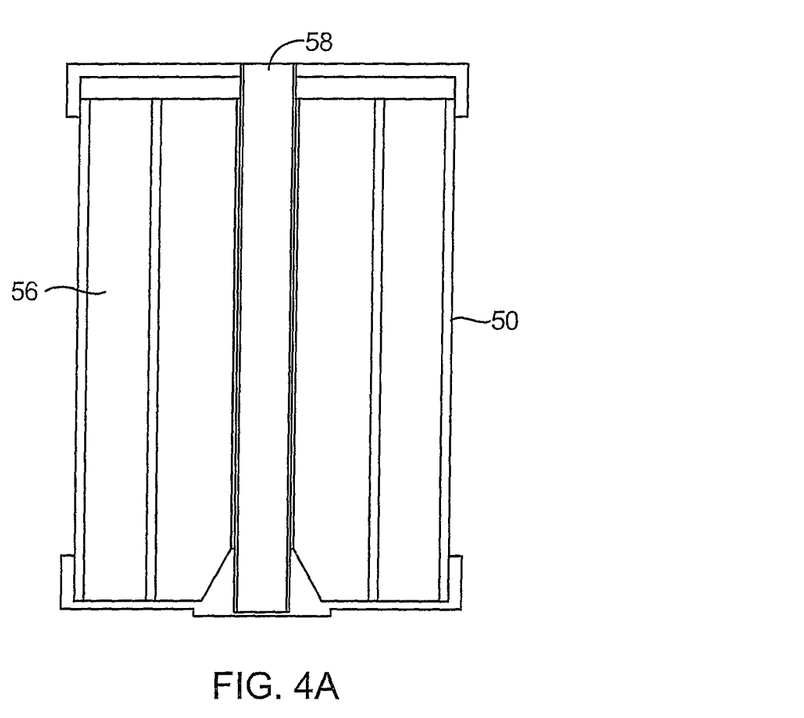
FIG. 4A is a cross-sectional view of a containment vessel, or cannister.
Figure 4B:
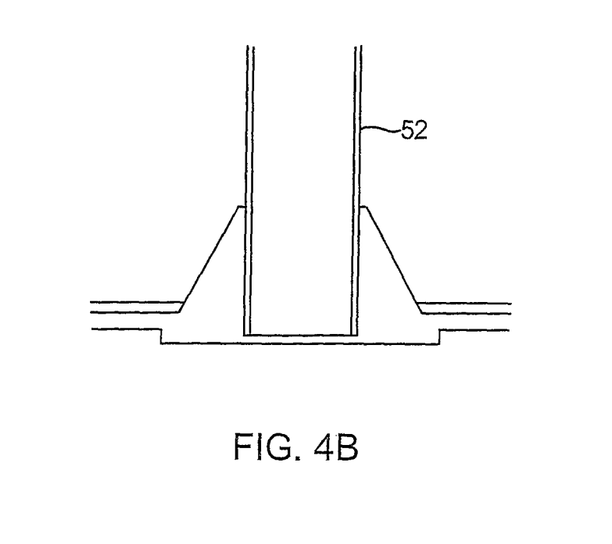
FIG. 4B is a close-up view of the center, bottom of the cross-sectional view of the containment vessel to more clearly show the heat cartridge sleeve of the containment vessel.

Referring to FIG. 4A, in one embodiment the reaction chamber 20 may be configured to allow for a heating element 58, or cartridge, extending axially along the containment vessel 50. Referring to FIG. 4B, the containment vessel 50 may also include a heat cartridge sleeve 52 to accommodate the heating element 58, or cartridge.

In one embodiment the formulation for the reactants may include the following: approximately 2.3 kg of calcined chromium oxide ($Cr_2O_3$) or approximately 51% of the granulation, approximately 1.6 kg of sodium nitrite ($NaNO_2$) or approximately 34.7% of the granulation, and approximately 0.65 kg of sodium nitrate ($NaNO_3$) or approximately 14.4% of the granulation. These amounts can be adjusted to provide an optimal production of nitric oxide. Generally, the amounts for the respective components may be adjusted plus or minus 10% of the granulation.

Calcined products are best stored under vacuum. The components are best ground to produce a loose granulation passing through a 5 micron screen. Each of the components should go through a double grind separately. All the components should be ground together a third time. The resulting granulation should be stored under nitrogen ($N_2$) or under vacuum at a comparatively cooler temperature than room temperature (lower is better) and in low light or no light conditions.

In one embodiment, the concentration of nitric oxide delivered can be varied anywhere from 0 ppm to one million ppm. Principally, the nitric oxide may be diluted with outside air. However, the system may be configured such that the nitric oxide can be diluted with any designated gas. Excess gas or nitric oxide can be vented to the atmosphere. The concentration can be adjusted rapidly in order to respond to the protocols and parameters of a variety of nitric oxide therapies.

Figure 5:
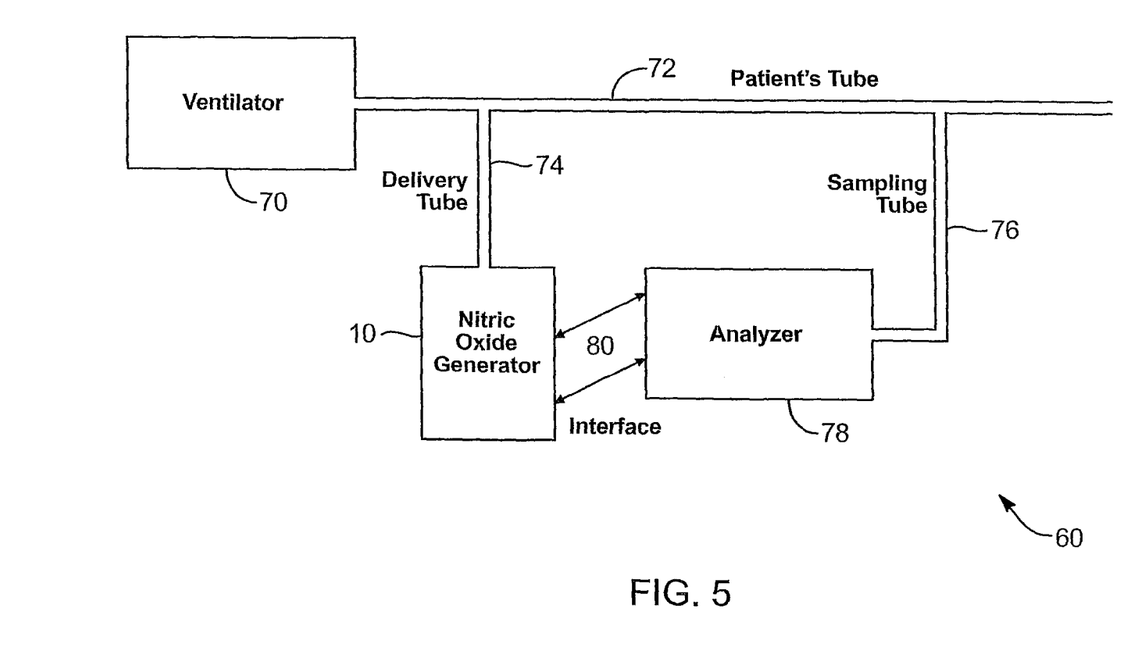
FIG. 5 is a schematic view of an automated feedback system that can monitor and adjust the flow or concentration of nitric oxide provided to a ventilator system.

Referring to FIG. 5, in one embodiment, an integrated system 60 may be utilized to control and adjust the delivery of nitric oxide. Such a system may sample or measure the concentration of nitric oxide delivered to a user and then automatically adjust the amount of nitric oxide delivered to the air flow of the user. For example and not by way of limitation, a nitric oxide therapy may be delivered to a patient using a ventilator 70 with a breathing tube 72. After the nitric oxide is delivered to the air flow in the breathing tube through a delivery tube 74, a sample is taken through a sampling tube 76, or the air flow is measured, to determine the concentration of nitric oxide. Any device suitable for analyzing 78 or measuring the concentration of nitric oxide may be used. After a determination is made with regard to the concentration of nitric oxide, the amount of nitric oxide delivered to the air flow in the breathing tube can be adjusted by adjusting the controls of the nitric oxide dilution apparatus, such as adjusting the speed of the pumps or a bypass air inlet in the apparatus.

In one embodiment, an integrated system 60 includes a feedback loop. Measuring, adjusting, and controlling the concentration of nitric oxide may be monitored and controlled by an interface 80 device.

Again referring to FIG. 1, one embodiment of an apparatus and method in accordance with the invention may rely on a series of process steps constituting a method or process. For example, providing a pump may involve any one or more of the required tasks of identifying materials and determining the structural and mechanical characteristics for such a pump. Accordingly, providing a pump may involve design, engineering, manufacture and acquisition of such a device. Similarly, providing a potentiometer to control a pump by varying the voltage or current to the pump may involve identifying materials and determining the structural and mechanical characteristics for such a potentiometer. Accordingly, providing a potentiometer may involve design, engineering, manufacture, and acquisition of such a device.

Providing an activated carbon filter may involve identifying materials, selecting a shape, selecting a cross-sectional profile and active area, and determining the structural and mechanical characteristics for such a filter. Similarly, providing a calcium hydroxide filter may involve identifying materials, selecting a shape, selecting a cross-sectional profile, evaluating an active area, and determining the structural and mechanical characteristics for such a filter. Accordingly, providing any type of filter may involve design, engineering, manufacture and acquisition of such a device.

Providing a reactor may involve selection of materials, selection of a profile and of cross-sectional area, engineering, design, fabrication, acquisition, purchase, or the like of a reactor in accordance with the discussion hereinabove.

Providing reactants may include selection of reacting species, selecting a configuration, such as granules, powder, liquid, gel, a solution, multiple components to be mixed, or the like. Likewise, the particular configuration of a solidous configuration of reactants may involve selecting a sieve size for the particles. This size can affect surface area available to react, heat penetration distances, and times controlling overall chemical reaction rates. Thus, selecting or otherwise providing reactants for the reactor may involve consideration of any or all aspects of chemistry, reaction kinetics, engineering, design, fabrication, purchase or other acquisition, delivery, assembly, or the like.

Assembling the apparatus may also include the disposition of reactants within various locations within a reactor, system, or the like as discussed hereinabove.

Activating the reactants in the reactor may involve, either adding a liquid, mixing the reactant components together, dispersing individual reactants in respective solutes to provide solutions for mixing, adding a liquid transport carrier to dry ingredients in order to initiate exchange between reactants, heating the reactants, a combination thereof, or the like.

Likewise, activation of the reactants may also involve opening valves, opening seals, rupturing or otherwise compromising seals as described hereinabove, or otherwise moving or manipulating reactants with or without carriers in order to place them in chemical and transport contact with one another.

In certain embodiments, nitric oxide may be separated from the reactants themselves. For example, the concept of a molecular sieve as one mechanism to separate nitric oxide form other reactants and from other species of nitrogen compounds is possible. In other embodiments, pumps, vacuum devices, or the like may also tend to separate nitric oxide. Accordingly, in certain embodiments, a suitably sized pump may actually be connected to the reactor in order to draw nitric oxide away from other species of reactants or reacted outputs.

Conducting therapy using nitric oxide may involve a number of steps associated with delivery and monitoring of nitric oxide. For example, in certain embodiments, conducting therapy may involve activating a reactor or the contents thereof.

Monitoring may involve adding gauges or meters, taking samples, or the like in order to verify that the delivery of nitric oxide from the reactor to the user does meet the therapeutically designed maximum and minimum threshold requirements specified by a medical professional.

Ultimately, after the expiration of an appropriate time specified, or the exhaustion of a content of a reactor, a therapy session may be considered completed. Accordingly, the apparatus may be removed from use, discarded, or the like. Accordingly, the removal or discarding of the apparatus may be by parts, or by the entirety.

It is contemplated that the reactor may typically be a single dose reactor but need not be limited to such. Multiple-dose or reusable reactors may also be used. For example, the reactor may actually contain a cartridge placed within the wall. The internal structure of the cartridge may be ruptured in the appropriate seal locations, such as by a blade puncturing the seals by a mechanism on, in, or otherwise associated with the main containment vessel or wall, and thus activated. Accordingly, the reactor may be reused by simply replacing the cartridge of materials containing the reactant volumes.

A patient may also obtain the benefits of nitric oxide therapy by utilizing a topical application that generates nitric oxide. The nitric oxide may affect the surface to which the topical application is applied, and may be absorbed by a surface such as skin.

Figure 6:
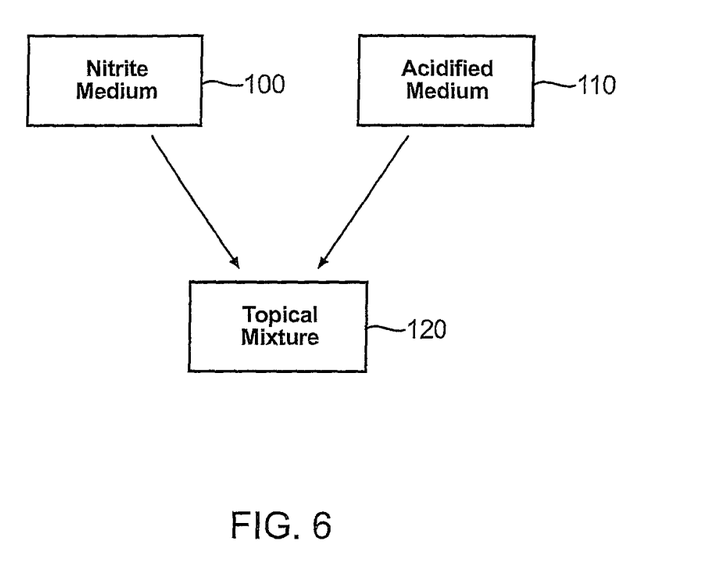
FIG. 6 is a schematic of a possible combination a nitrite medium and an acidified medium for production of a topical medium for topical application of nitric oxide therapy.

Referring to FIG. 6, two individual, separate, component media are provided. The first medium is a nitrite medium 100 and generally provides the nitrite reactants in some suitable form described herein above, such as sodium nitrite, potassium nitrite, or the like. The second medium is an acidified medium 110 and generally provides at least one acidic reactant in some suitable form, such as citric acid, lactic acid, ascorbic acid, or the like. Reaction rate and pH control are best achieved by using a mixture of multiple food-grade acids. When approximately equal amounts of the two individual components (media) are combined into a topical mixture 120, a reaction is initiated that produces nitric oxide.

Two containers may be provided, each container is capable of dispensing a suitable amount of a given medium (one of the two to be mixed). The containers may be identical in structure and composition, but need not necessarily be so. The containers may dispense the medium by a pump action, such as is common with lotions and soaps. The containers may dispense the medium by a squeezing or shaking action, such as is common with viscous or thixotropic shampoos, condiments, colloidal suspensions, gels, and other compositions.

The medium may be any suitable medium for containing and dispensing the reactants, for example, the medium may be a gel or a lotion. A gel may be obtained by including a water-soluble polymer, such as methyl cellulose available as Methocel™, in a suitable solution. A lotion used to suspend the reactants for a nitrite lotion medium and an acidified lotion medium may be selected such as the Jergens® brand hand and body lotion. For best results, the media holding a matched pair of reactants should be essentially the same. The chemical characteristics of the media may not be strictly identical, but the physical compositions should be essentially the same so as to mix readily and not inhibit the reaction.

For example, a nitrite gel medium may have a slightly acidic to neutral pH while an acidified gel medium may have a more acidic pH than the corresponding nitrite gel medium. Using a nitrite gel medium with an acidified lotion medium may not provide optimal results. Using different media may not provide the best rates for desired results, but would probably not be dangerous.

Generally, a topical application of nitric oxide may be provided by mixing equal amounts of a nitrite medium 100 and an acidified medium 110. The mixture 120 is then applied to the intended surface. The mixture 120 may be applied to a person's skin, or even an open wound.

The mixture 120 provides nitric oxide to the intended surface. As the nitrite medium 100 is mixed with the acidified medium 110, the reduction of nitrite by the acid(s) leads to the release of nitric oxide. The exposure to nitric oxide may serve a variety of purposes.

A topical mixture 120 that produces nitric oxide may be used for antimicrobial, antifungal, or similar cleaning purposes. Infectious diseases are caused by pathogens such as bacteria, viruses, and fungi. Antibacterial soaps can kill some bacteria, but not necessarily all bacteria. A topical mixture as described has been shown to kill as many as, and more, bacteria compared to commercially available antibacterial soaps or hospital-based instant hand antiseptics.

A topical mixture 120 that produces nitric oxide may be used for localized analgesic purposes. The analgesic effect nitric oxide may be provided via topical application.

A topical mixture 120 that produces nitric oxide may be used for anti-inflammatory purposes. A topical mixture that produces nitric oxide may also be used to disperse a biofilm. Biofilms are colonies of dissimilar organisms that seem to join symbiotically to resist attack from antibiotics. Nitric oxide signals a biofilm to disperse so antibiotics can penetrate the biofilm. It is also believed that nitric oxide interferes with the uptake of iron.

A topical mixture 120 that produces nitric oxide may be used to help heal various kinds of wounds. Tests have been performed wherein a topical mixture that produces nitric oxide as described herein is applied regularly to an open wound that is generally resistant to healing. The wound was seen to show significant healing within a few weeks.

For example, a person in Canada had poor circulation and unresponsive diabetic ulcers on the person's feet. The person was immobilized and in a wheel chair, and had been scheduled for amputation to remove the person's foot about a month after this experiment began. A topical mixture 120 that produces nitric oxide was applied to the diabetic ulcers once a day. The person soaked the effected foot in a footbath solution that produces nitric oxide for approximately twenty minutes once every four days. Within two weeks the person was able to walk and go out in public. Within 4-6 weeks, the person was mobile and had achieved a substantially complete recovery. Meanwhile, the scheduled amputation was cancelled.

It was shown that a topical mixture that produces nitric oxide will kill squamous cells, pre-cancerous cells, if the concentration of nitric oxide is high enough. Tests intending to show that a topical mixture that produces nitric oxide would grow hair based in part on the increase of blood flow that accompanies application of nitric oxide actually showed that nitric oxide in as high doses provided as described herein above did kill squamous cells.

The nitrite medium 100 may be formulated in any suitable medium and the concentration of reactants can be adjusted as desired as long as the intended reaction and sufficient concentrations of nitric oxide is obtained. For example, a suitable tank may be charged with distilled/deionized water (94.94% w/w) at room temperature (20°-25° C.). Sodium nitrite (3.00% w/w) and Kathon CG (0.05% w/w) may be dissolved in the water. Methocel™ (HPMC, cold dispersable; 1.75% w/w) may be stirred into the water until no lumps are present. Sodium hydroxide (10N to approximately pH 8; 0.09% w/w) may be rapidly stirred into the water to thicken, and care should be taken to avoid trapping air bubbles that can occur as a result of higher shear mixing.

EDTA, Na4 salt (0.10% w/w) may be stirred into the water until dissolved. Citric acid (crystalline; 0.08% w/w) may be added to adjust the mixture to a pH of 6.0. Small quantities of sodium hydroxide may be used to adjust the pH as needed. The individual percentages may be adjusted as desired for the best results.

The acidified medium 110 may be formulated in any suitable carrier and the concentration of the reactants can be adjusted as desired as long as the intended reaction and sufficient concentrations of nitric oxide are obtained. For example, a suitable tank may be charged with distilled/deionized water (89.02% w/w) at room temperature (20°-25° C.). Kathon CG (0.05% w/w) may be dissolved in the water. Methocel™ (HPMC, cold dispersable; 1.75% w/w) may be stirred into the water until no lumps are present. Sodium hydroxide (10N to approximately pH 8; 0.09% w/w) may be rapidly stirred into the water to thicken, and care should be taken to avoid trapping air bubbles that can occur as a result of higher shear mixing.

EDTA, Na4 salt (0.10% w/w) may be stirred into the water until dissolved. Stirring may continue until the Methocel™ is completely hydrated. Lactic acid (85% liquid solution; 3.00% w/w) and ascorbic acid (USP, crystalline; 3.00% w/w) may be stirred in until completely dissolved. Citric acid (crystalline; 3.00% w/w) may be added to adjust the mixture to a pH of 6.0. Small quantities of sodium hydroxide may be used to adjust the pH as needed. The individual percentages may be adjusted as desired for the best results.

The use of at least two acids in producing the acidified medium 110 may improve the shelf life of the acidified medium 110. Generally maintaining a pH of from about 3 to about 5 or above (so long as not too caustic for skin) has been found very useful in maintaining the shelf life of the product.

A topical mixture 120 that produces nitric oxide has been shown to be effective in cleaning and disinfecting hands. For example, three sets of volunteers, with approximately 26 people in each set, participated in a test to determine the effectiveness of nitric oxide as a cleaning and disinfecting agent. The right and left hands of each person in each set of volunteers were swabbed with cotton-tipped applicators prior to any type of washing. The applicators were plated onto nutrient blood agar petri dishes using the three corner dilution method.

Each set of volunteers washed their hands using separate soaps for washing. The first set of volunteers washed their hands for thirty (30) seconds using a topical mixture 120 of equal parts of nitrite gel medium and acidified gel medium as described herein above. The second set of volunteers washed their hands for thirty (30) seconds using a commercial antibacterial agent Avagard™D. The third set of volunteers washed their hands for fifteen (15) seconds using Dial™ Complete Foaming Hand Wash, and then rinsed for fifteen (15) seconds and dried.

The right and left hands of each person in each set of volunteers were swabbed again with cotton-tipped applicators after washing. The applicators were plated onto nutrient blood agar petri dishes using the three corner dilution method. All the blood agar petri dishes were incubated for forty-eight (48) hours at 35° C. The results were tabulated based on a grading scale of bacteria colonization. The testing showed that a topical mixture that produces nitric oxide reduced the relative bacterial content by approximately 62%. Avagard™D reduced the relative bacterial content by approximately 75%. Dial™ Complete Foaming Hand Wash reduced the relative bacterial content by approximately 33%. Thus, a topical mixture that produces nitric oxide was found to be approximately twice as effective and cleaning and disinfecting hands than Dial™ Complete Foaming Hand Wash and almost as effective as Avagard™D.

It has been determined that the dose required to kill bacteria on a surface, such as a person's skin, is at least approximately 320 ppm of nitric oxide. A topical gel mixture of approximately three (3) grams of nitrite gel medium and approximately three (3) grams of acidified gel medium that produces nitric oxide has been shown to deliver approximately 840 ppm of nitric oxide. Similarly, a topical gel mixture of approximately three (3) grams of nitrite lotion medium and approximately three (3) grams of acidified lotion medium that produces nitric oxide has been shown to deliver approximately 450 ppm of nitric oxide.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A method of generating nitric oxide, the method comprising:
   pumping a filtered gas into a reaction chamber, wherein the filtered gas is ambient air that has been filtered to remove oxygen and moisture;
   providing a mixture of reactants in a solid form comprising at a mixture of a calcined chromium oxide compound in combination with, a nitrite compound and a nitrate compound in the reaction chamber;
   activating the reactants to initiate a reaction generating a nitric oxide gas without the use of a liquid or a solution;
   evacuating the nitric oxide gas away from the reaction chamber in a closed conduit to inhibit further heating thereof and to resist further reaction of the nitric oxide gas;
   filtering the nitric oxide gas after the reaction; and
   delivering the nitric oxide at substantially ambient conditions to a user to provide a therapeutically safe concentration of nitric oxide.

2. The method of claim 1, wherein the reactants are activated by use of a heating element connected to the reaction chamber.

3. The method of claim 1, further comprising:
   cooling the nitric oxide gas after it is evacuated from the reaction chamber.

4. The method of claim 1, further comprising:
   analyzing the concentration of the nitric oxide gas being delivered to the user; and
   adjusting the concentration of the nitric oxide gas being delivered to the user via an automated feedback loop to maintain a desired concentration.

5. A method for producing nitric oxide gas comprising:
   pumping a filtered gas into a reaction chamber, wherein the filtered gas is ambient air that has been filtered to remove oxygen and moisture;
   providing a granulated mixture of reactants, wherein the granulated mixture comprises effective amounts of calcined chromium oxide, a nitrite compound, and a nitrate compound and the granulated mixture is capable of passing through a five micron screen and capable of producing a nitric oxide gas in the reaction chamber, wherein the granulated mixture of reactants are activated by use of a heating element connected to the reaction chamber;
   activating the reactants and generating the nitric oxide gas;
   evacuating the nitric oxide gas away from the reaction chamber in a closed conduit to inhibit further heating thereof and to resist further reaction of the nitric oxide gas; and
   delivering the nitric oxide at substantially ambient conditions to a user to provide a therapeutically safe concentration of nitric oxide.

6. The method of claim 5, further comprising:
   cooling the nitric oxide gas after it is evacuated from the reaction chamber.

7. The method of claim 6, further comprising:
   filtering the nitric oxide gas after it is evacuated from the reaction chamber.

8. The method of claim 6, further comprising:
   analyzing the concentration of the nitric oxide gas being delivered to the user; and
   adjusting the concentration of the nitric oxide gas being delivered to the user via an automated feedback loop to maintain a desired concentration.

9. A method for producing nitric oxide gas comprising:
   pumping a filtered gas into a reaction chamber;
   providing a mixture of at least three reactants in the reaction chamber, wherein the mixture is in a solid form and comprises at least a calcined chromium oxide compound, a nitrite compound, and a nitrate compound;
   activating the reactants and generating a nitric oxide gas;
   evacuating the nitric oxide gas away from the reaction chamber in a closed conduit to inhibit further heating thereof and to resist further reaction of the nitric oxide gas;
   cooling the nitric oxide gas;
   filtering the nitric oxide gas;
   analyzing the concentration of the nitric oxide gas;
   adjusting the concentration of the nitric oxide gas; and
   delivering the nitric oxide at substantially ambient conditions and at the adjusted concentration to a user.

10. The method of claim 9, wherein the reactants are activated by use of a heating element connected to the reaction chamber.

* * * * *